United States Patent
Harper et al.

(10) Patent No.: US 6,219,442 B1
(45) Date of Patent: Apr. 17, 2001

(54) APPARATUS AND METHOD FOR MEASURING DISTORTION OF A VISIBLE PATTERN ON A SUBSTRATE BY VIEWING PREDETERMINED PORTIONS THEREOF

(75) Inventors: Benny Michael Harper; Pieter J. M. Kerstens, both of Boca Raton; Jon Rowlan Shumate, Boynton Beach; John Lennon Sullivan, Boca Raton, all of FL (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 08/727,199

(22) Filed: Oct. 8, 1996

(51) Int. Cl.[7] .................................................. G06K 9/00
(52) U.S. Cl. .................... 382/141; 382/145; 382/148; 382/151; 348/87; 348/153
(58) Field of Search .................... 382/141, 145, 382/144, 148, 149, 199, 151, 152, 165, 181; 348/87, 153

(56) References Cited

U.S. PATENT DOCUMENTS

| | | | |
|---|---|---|---|
| 4,581,762 | * | 4/1986 | Lapidus et al. ........................ 382/22 |
| 4,618,938 | * | 10/1986 | Sandland et al. ..................... 364/552 |
| 4,857,752 | * | 8/1989 | Hara et al. ........................... 382/145 |
| 4,982,438 | * | 1/1991 | Usami et al. .......................... 382/1 |
| 5,060,065 | | 10/1991 | Wasserman ........................... 358/106 |
| 5,113,565 | * | 5/1992 | Cipolla et al. ........................ 358/101 |
| 5,260,779 | * | 11/1993 | Wasserman ........................... 382/147 |
| 5,335,293 | * | 8/1994 | Vannelli et al. ....................... 382/17 |
| 5,495,337 | * | 2/1996 | Goshorn et al. ..................... 348/126 |
| 5,638,461 | * | 6/1997 | Fridge ................................. 382/141 |
| 5,668,665 | * | 9/1997 | Choate ................................ 359/663 |
| 5,703,784 | * | 12/1997 | Pearson .............................. 364/487 |
| 5,717,780 | * | 2/1998 | Mitsumune et al. ................. 382/100 |
| 5,825,483 | * | 10/1998 | Michael et al. .................... 356/243.1 |

* cited by examiner

Primary Examiner—Matthew C. Bella
Assistant Examiner—Sheela Chawan
(74) Attorney, Agent, or Firm—Ronald V. Davidge; Richard A. Tomlin (57) ABSTRACT

An inspection station for determining the characteristics of a visible overlay pattern on a ceramic substrate includes an electronic camera unit directed at each corner of the overlay pattern. The inspection station is calibrated using a calibration substrate having a known pattern, portions of which are viewed by the cameras. The cameras remain stationary during both the calibration process and during the subsequent inspection of one or more substrates. In a first version of the station, a holder holding the substrate in place is split into quadrants, which are moved with associated camera units to accommodate varying sizes of rectangular substrates. In a second version, a lens is added to increase the magnification of the optical path to the camera units.

9 Claims, 4 Drawing Sheets

APPARATUS AND METHOD FOR MEASURING DISTORTION OF A VISIBLE PATTERN ON A SUBSTRATE BY VIEWING PREDETERMINED PORTIONS THEREOF

BACKGROUND OF THE INVENTION

1. Field of the Invention

This invention relates to the inspection of overlays on substrates, and, more particularly, to a method for performing a partial inspection likely to identify defective parts.

2. Background Information

In a number of electronic circuit chips, I/O (Input/Output) connections from the various internal circuits are made through ceramic substrates extending along the bottom surface of the chip. Each ceramic substrate has an external surface with an external overlay pattern of conductive pads to which external conductors, such as pins, are attached, for example, by brazing, and an internal overlay pattern of conductive pads to which internal connections from the circuits are made, for example, by reflowing very small solder balls.

The process of manufacturing the ceramic substrate includes the lamination of a number of ceramic layers, each of which carry conductive traces extending among various of the conductive pads. Some of these conductive traces extend between individual pads of the internal and external overlay patterns. After the overlay patterns are placed on the ceramic substrate, the substrate is cured in an oven. Since the curing process causes the substrate to shrink, the overlay pattern is applied in a stretched, or oversized configuration. However, the ceramic substrate, and hence the overlay pattern may shrink at a different rate than that which has been predicted, causing the overlay pattern to be too large or too small, or the shrinkage may be uneven, causing the overlay pattern to be distorted. It is therefore necessary to inspect overlay patterns after the process of curing the substrate.

The conventional method for inspecting overlay patterns on substrates uses a camera to determine the dimensions of the substrates, the distortion of the overlay pattern, the position of this pattern on the substrate, and the feature sizes of the pattern. Since the complexity of the overlay pattern exceeds the resolution of the camera system and/or the memory capacity of an associated computer system if an attempt is made to view the entire overlay pattern at once, the pattern is viewed sequentially in a number of portions according to a co-ordinate system. This method requires that either the substrate being examined or the camera be moved among many positions to acquire the data needed to inspect the substrate. Because of this movement, the inspection process is both complicated, requiring an expensive inspection tool, and slow, requiring typically 90 seconds per part inspected.

What is needed is a way to perform essential inspection procedures without the complexity of moving a camera among sequentially-viewed portions of the overlay pattern, or of moving the part being inspected to present various portions thereof to the camera.

SUMMARY OF THE INVENTION

In accordance with one aspect of the invention, there is provided apparatus for determining characteristics of a visible pattern on a substrate during an inspection process. The apparatus includes a holder holding the substrate stationary during the inspection process, a number of camera units aimed at the visible pattern, and a computer responsive to an output signal from each of the camera units. Each of the camera units is aimed at a different field of view, with the various fields of view being spaced apart from one another. Each camera unit is held stationary during the inspection process. The computer determines whether features of the visible pattern are within pre-determined limits.

DETAILED DESCRIPTION

Figure 1:
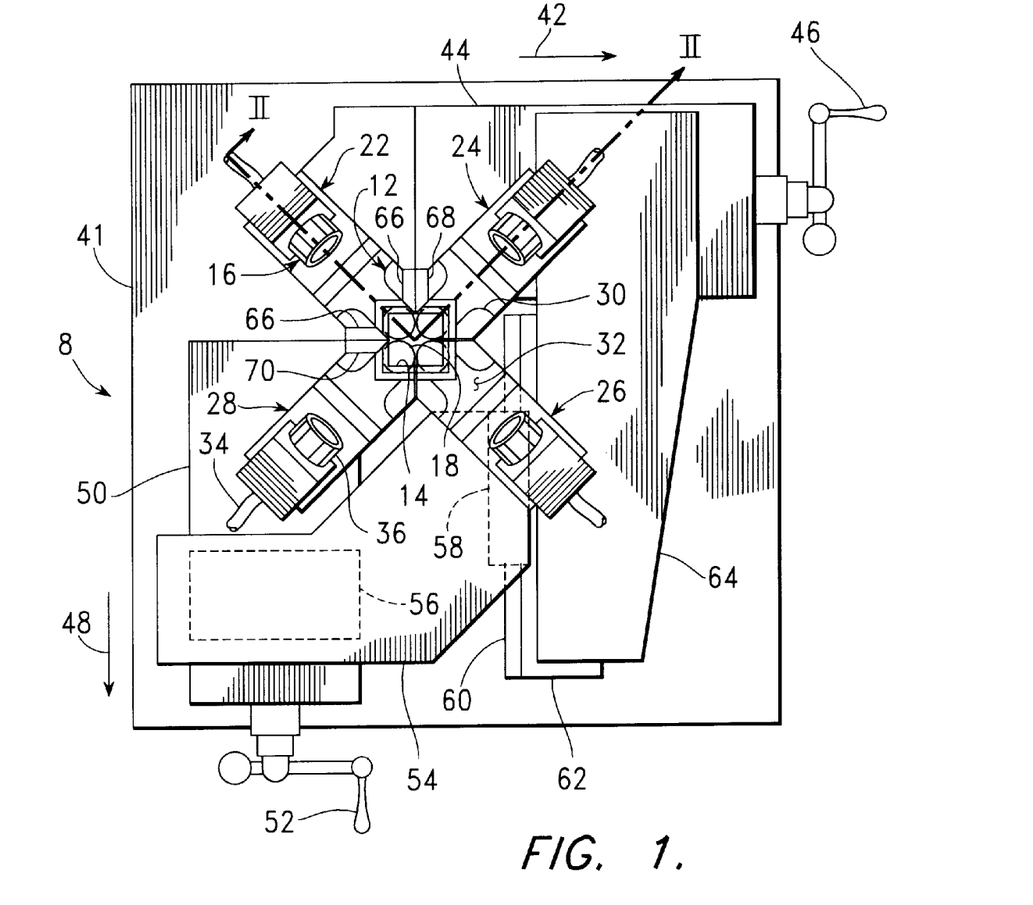
FIG. 1 is a plan view of an inspection station built in accordance with a first embodiment of the present invention.
Figure 2:
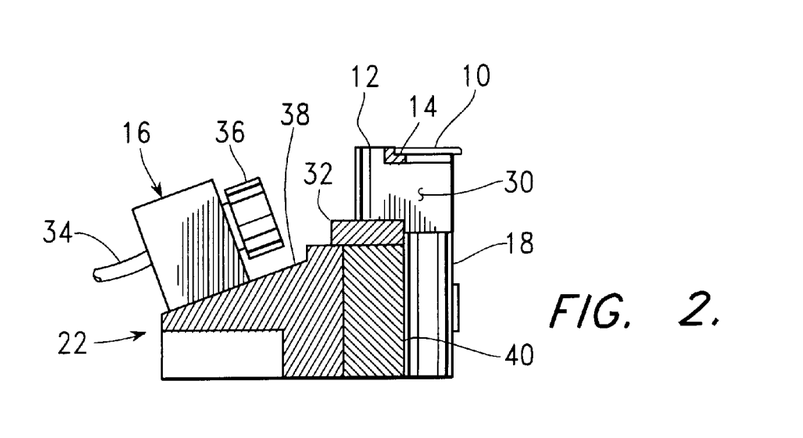
FIG. 2 is a vertical cross-sectional view of the apparatus of FIG. 1, taken as indicated by section lines II—II in FIG. 1.

FIG. 1 is a plan view of an inspection station 8 built in accordance with a first embodiment of the present invention, and FIG. 2 is a vertical cross-sectional view of the apparatus of FIG. 1, taken as indicated by section lines II—II in FIG. 1. This embodiment of the present invention is configured particularly for inspecting the external overlay pattern, which extends almost entirely along the external surface of the substrate.

The substrate 10, which, for clarity, is shown in FIG. 2 but not in FIG. 1, is placed atop four corner support structures 12, each of which includes a notched ledge 14 supporting a corner of the substrate 10 during the inspection process. The substrate 10 is placed atop the corner support structures 12 with the pattern to be inspected facing downward to be illuminated by four light sources 16 and viewed by four upward-facing camera units 18.

A support structure 12, a light source 16, and a camera unit 18, are fastened together with support hardware to form an individual inspection assembly 22, 24, 26, 28 associated with a corner of the substrate 10 to be inspected. Each support structure 12 includes a pair of side walls 30 extending upward to the notched ledge 14 from a base 32. Each light source 16 includes a bifurcated fiber optic cable 34 extending to a lens assembly 36, transmitting light from a 150-watt halogen lamp (not shown). Each light source 16 is mounted on a sloped mounting block 38, which aims the illumination at the underside of the substrate 10. Each camera unit 18 is clamped to a mounting block 40.

The inspection assemblies 22, 24, 26, 28 are mechanically tied together to perform movements specifically needed to accept rectangular substrates 10 of varying dimensions. As shown in FIG. 1, the inspection assemblies 22, 24, 26, 28 are in their closest together configuration, with camera units 18 nearly touching, as required to inspect the smallest square substrate. Rear left inspection assembly 22 is stationary, being rigidly mounted to a base plate 41. Rear right inspection assembly 24 is moved from the position of FIG. 1 in the X-direction indicated by arrow 42, being attached to an X-direction slide 44, which is manually moved in the direction of arrow 42, and opposite thereto, by turning a handcrank 46. Similarly, front left inspection assembly 28 is moved from the position of FIG. 1 in the Y-direction indicated by arrow 48, being attached to a Y-direction slide 50, which is manually moved in the direction of arrow 48, and opposite thereto, by turning a handcrank 52.

Front right inspection assembly 26 is attached to a mounting plate 54, which is moved in and opposite to the Y-direction of arrow 48 by means a slide 56 having an upper portion (not shown) attached to the mounting plate 54 and a lower portion (also not shown) attached to the moving part of Y-direction slide 50. The mounting plate 54 is also attached to a bushing block 58, which slides on a cylindrically curved portion 60 of a guide rail 62 attached to a bracket 64 extending from the moving portion of X-direction slide 44. In this way, the mounting plate 54, and hence the inspection assembly 26, is mounted to move in and opposite the X-direction of arrow 42 with X-direction slide 44, and hence with rear right inspection assembly 24, and in and opposite the Y-direction of arrow 48 with Y-direction slide 50, and hence with front left inspection assembly 28. This motion provides the inspection assemblies 22, 24, 26, 28 with all of the movements necessary to capture the corners of various rectangular substrates 10 within their ranges of motion.

The various slides 44, 48, 56 and bushing block 58 are of types well known to a person skilled in the art of designing various types of machine tools and inspection devices, and hence are not described in detail here. These devices may employ interlocking surfaces, such as dovetail joints between the stationary and sliding portions, or anti-friction devices, such as balls or rollers recirculating in channels may be used provide sliding motion in a preferred direction.

Continuing to refer to FIG. 1, a pair of stationary stops 66 attached to the stationary rear left inspection assembly 22 provide surfaces against which the substrate 10 is loaded by the operator. An additional moving stop 68, attached to the rear right inspection assembly 24 and moving therewith in the X-direction of arrow 42 from the position in which it is shown, and an additional moving stop 70, attached to the front left inspection assembly 28 and moving therewith in the Y-direction of arrow 48 from the position in which it is shown, are further provided to assist in the manual alignment of the substrate 10.

Figure 3:
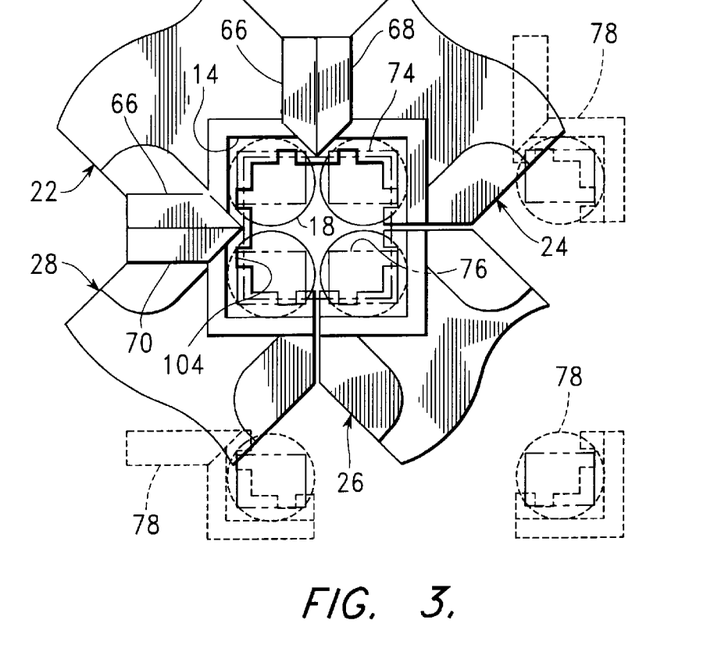
FIG. 3 is a fragmentary plan view of the central portion of the inspection station of FIG. 1.

FIG. 3 is a fragmentary plan view of the central portion of the inspection station 8 of FIG. 1, showing particularly the effects of adjusting the apparatus for different sizes of substrates on the mechanism for aligning the substrate with the apparatus and on the areas imaged by the four camera units 18. As described above in reference to FIG. 1, the stationary rear left inspection assembly includes a pair of stationary stops 66, against which a ceramic substrate is placed for inspection. The location of a minimum-sized substrate is indicated by phantom lines 74. Each camera 18 has a field of view indicated by phantom lines 76. The substrate is further held in place by a notched frame 14, which is moved apart as four separate corners to facilitate the insertion of a larger substrate when the inspection assemblies 24, 26, 28 are moved away from stationary inspection assembly 22 as described in detail in reference to FIG. 1.

The dashed lines 78 indicate the positions of the movable portions of notched frame 14, camera units 18, and fields of view 74 when these movable inspection assemblies 24, 26, and 28 are moved maximum distances from the stationary inspection assembly 22. Each camera unit 18 may be, for example, a Panasonic GP-MS112 ½-inch CCD camera 18 having a 682×492 pixel array and a 15 mm fix focal length lens with a polarization filter. With this configuration, each camera unit 18 has an 8.4 mm by 6.3 mm field of view of the substrate 10. Each camera unit has a 9.3 micron horizontal by 9.6 micron vertical pixel size, providing 3-sigma measurement accuracies for the diameter of a pad in the overlay pattern within ±5 microns, for the location of one pattern feature to another within ±15 microns, and for the location of a pattern feature to a feature, such as an edge, of the ceramic substrate within ±15 microns.

Movable stops 68 and 70 move with the inspection assemblies 24 and 28, to which they are respectively attached, so that two aligned stop positions are provided along adjacent sides for the positioning of relatively large substrates. Using this arrangement, an exemplary version of the inspection station 8 has handled substrates from 21 mm square up to 52 mm square.

Since the camera units 18 and their respective viewing areas 76 move with the inspection assemblies 24, 26, 28, the corner portions of a substrate are always viewed during the inspection process. Even when these inspection assemblies are moved together to hold the minimum size substrate, the central portion of the substrate is not viewed. This method of viewing is both efficient and sufficient, because the types of distortion of the overlay pattern which are likely to occur in the process of manufacturing a substrate, such as too much or too little shrinkage, or uneven shrinkage, in the curing process, effect the relative position of pads in the pattern at the four corner areas of the substrate. Furthermore, data obtained from the corners indicates whether the overlay pattern was properly aligned with the edges of the substrate.

Figure 4:
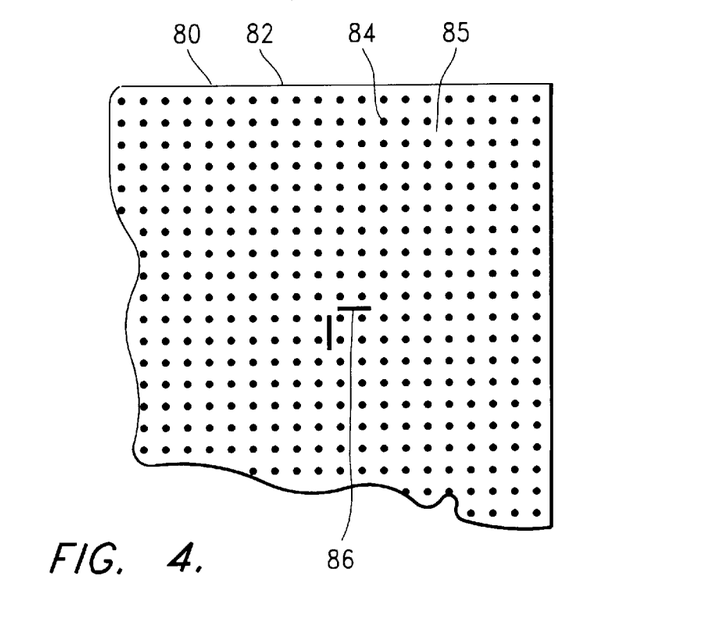
FIG. 4 is a fragmentary plan view of a calibration substrate used to calibrate the inspection station of FIG. 1.

FIG. 4 is a fragmentary plan view of a calibration substrate 80 used to calibrate the inspection station 8 of FIG. 1 with the inspection assemblies 24, 26, 28 in a particular configuration. This calibration substrate 80 may be composed, for example, of a quartz or fused silica sheet 82 having 0.25 mm chromium filled circles 84 arrayed in a rectangular pattern on a surface 85 thereof with center-to-center distances of 0.50 mm. The calibration substrate 80 also includes location indicia 86 consisting of lines 1.00 mm long and 0.125 mm wide, with the location indicia 86 being located at a pre-determined distance from specific features of the substrate 80, such as the edges or center thereof.

Figure 5:
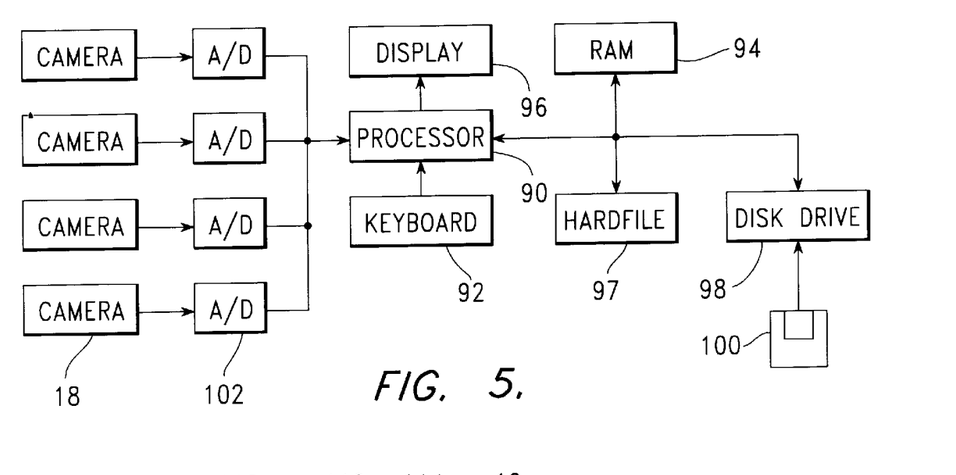
FIG. 5 is a block diagram of a computing system used to control inspection operations within the inspection station of FIG. 1.

FIG. 5 is a block diagram of a computing system used to control inspection operations within the inspection station 8 of FIG. 1, and to indicate the results of inspection operations. The computing system is of a conventional type, including a processor 90, a keyboard 92 for operator input, a system memory 94 holding data and operating instructions, typically in separate portions thereof, a display unit 96 providing visual indications, for example, of test results, a hardfile 97, and a diskette drive 98 reading magnetically recorded diskettes 100, which are used, for example, to provide a program, which, when loaded into system memory 94 and executed within processor 90, control operation of the inspection station. The output of each of the four camera units 18 is provided as an input to the processor through an analog to digital convertor 102.

Referring again to FIG. 1, the operation of the inspection station 8 to inspect a number of substrates of similar dimensions begins when the operator determines whether the movable inspection assemblies 24, 26, 28 have to be adjusted to accommodate the substrates to be inspected. If he determines that such an adjustment must be made, he performs the adjustment by turning handcranks 46, 52 as required.

Continuing to refer to FIG. 1, and referring additionally to FIGS. 4 and 5, whenever a new type of substrate is to be inspected, the calibration substrate 80 is used to establish a new calibration for the inspection station 8. During the calibration process, this substrate 80 is placed in notched frame 14, with the patterned surface 85 facing downward to be imaged by the camera units 18.

The calibration process begins when the program executing in processor 90 reads product reference information for the substrates to be inspected. For this reason, re-calibration is needed whenever a different type of substrate is to be inspected, even if it can be inspected without changing the positions of movable inspection assemblies 24, 26, 28. This information consists of a data set specific to a size of substrate and type of pattern to be inspected. This data set describes such parameters as the distance between pads and reference marks and allowable tolerances. Next, the illumination sources 16 are turned on and the calibration substrate 80 is imaged using the four cameras 18. Data from the calibration substrate 80 is used to provide scale to each of the four images from the camera units 18. The locations of the images formed by circles 84 are used to build a frame of reference for the image from each camera unit 18, with corrections being made for lens distortion, which can produce well-known barrel or pincushion effects, and for the angle at which the pixel pattern of the camera is aligned with respect to the pattern of circles 84 on the calibration substrate 80. In general, it is understood that the four camera units 18 are installed at slightly different angles with respect to each other and to the pattern of circles 84. The calibration processes may be performed using a modified version of the C-programmable Cognex 4400 box-version vision system. Thus, during this portion of the calibration process, the distortion characteristics of the optical system for each camera unit 18, including its lens, are mapped to develop a distortion transform function of each camera unit 18.

Next, in a final part of the calibration process, the calibration factors determined for each of the camera units 18 are used, together with data from the product reference information, to build a system frame of reference. In each camera image, the location of a single "L"-shaped indicia marking 86 is compared to its actual distance from the center of the calibration substrate 80. If two or more indicia markings 86 are visible within a single camera image, the one closest to the center of the camera image is used for this purpose. The pixel locations indicating the indicia marking 86 are corrected to represent the actual distances, in Cartesian co-ordinates, from a central datum of the calibration substrate 80. The correction factors applied to these pixel locations are similarly applied to other pixel locations of the individual camera image, so that distances from the center of a substrate can be accurately determined. Thus, during this portion of the calibration process, the four camera units 18 are calibrated into a single co-ordinate system, with the spacing and rotation of the individual camera units 18 being considered.

With the calibration process now complete, the operator removes the calibration substrate 80 from the inspection station 8, and replaces it with the first substrate 10 to be tested. Then he provides an input, for example, through the keyboard 92, requesting the system to inspect the substrate 10. In accordance with the program executing in processor 90, images are read from the four camera units 18. Next, the various features of the substrate 10 and overlay pattern, as listed in the product reference information, are measured, and the measurements of individual camera units 18 are related to the system frame of reference developed during the calibration process. The measurements made with individual camera units 18 are rotated to compensate for the individual camera angles determined in the calibration process. The placement of features is tested within the system frame of reference, with the placement of features measured by each of the four camera units 18 being compared with the location of features measured by the other three camera units to determine such parameters as the overall length and width of the overlay patten. The results of these measurements and calculations are compared with tolerance values from the product reference information. Various portions of the inspection process may also be performed using the Cognex 4400 box version vision system.

During this process, the location of features of the overlay pattern with respect to one another, such as the overall size of the overlay pattern, are considered, together with the location of the overlay pattern relative to the edges of the substrate 10. For example, the size of the substrate 10 is first determined by examining pixels in eight locations, each having a pre-determined offset from the adjacent corner. As shown in FIG. 3, if the substrate 10 is resting on a ledge of the notched frame 14, notches 104 in this ledge reveal the edge of the substrate 10 to the camera units 18. This method is used to avoid the interaction of chamfers and irregularities occurring at the corners of the substrate 10. The eight calculated edge positions resulting from these measurements are used to determine the location of the center of the substrate 10 and the angle at which the substrate 10 lies within the apparatus. This data on substrate geometry is then used to determine whether the overlay pattern is properly located.

Next, with the completion of the processes required to inspect an individual part, the results of the inspection are displayed on display unit 96. The indication presented may be as simple as "GOOD PART" versus "BAD PART," or specific reasons for failure or positioning of measurements within various tolerance bands may be reported. The inspection station 8 then preferably stores measurement data in hardfile 97 for subsequent additional analysis.

In both the calibration and inspection processes, output signals from the four camera units 18 may be examined simultaneously or sequentially. Sequential examination is needed particularly when the system memory 94 is inadequate to handle all of the data simultaneously. Even when images are handled sequentially, image processing is quite fast, with the image capture time taking about 200 milliseconds, and with vision processing taking about two seconds before the results are posted at the display unit 96. Thus, an inspection station built in accordance with the present invention has a significant throughput advantage over the background art method of moving a camera or substrate, which required about 90 seconds of inspection time.

While the first embodiment 8 shown in FIG. 1 is particularly useful for inspecting the external overlay pattern extending virtually across the external surface of a ceramic substrate, it is not well suited for inspecting the relatively small internal overlay pattern, which typically extends along a relatively small, centrally located portion of the inner surface of the ceramic substrate. With first embodiment 8, it is difficult or impossible to bring the camera units 18 close enough together to obtain a proper view of the smaller internal overlay pattern. Furthermore, since the features of the internal overlay pattern are also relatively small, additional magnification is needed to obtain an adequate resolution of the feature details.

Figure 6:
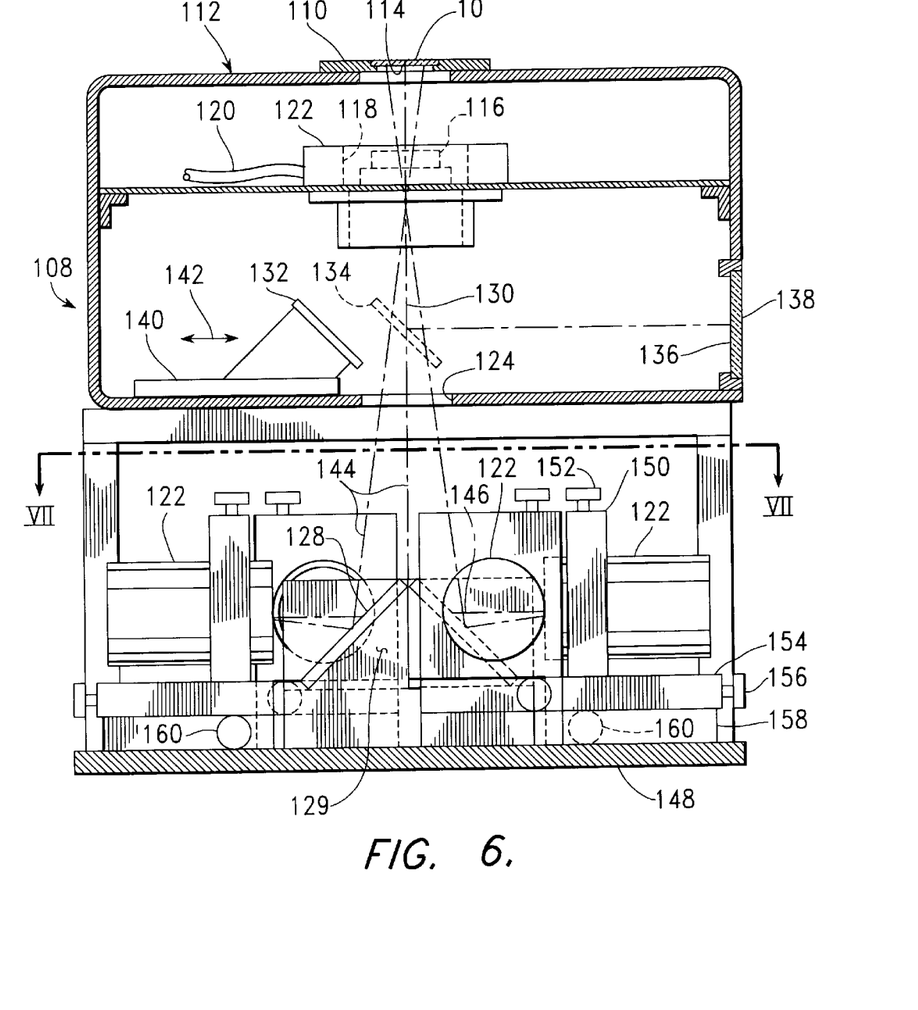
FIG. 6 is a partially sectional elevation of an inspection station built in accordance with a second embodiment of the present invention.

Therefore, a second embodiment of the present invention, which is configured particularly for inspecting the relatively small internal overlay pattern of a ceramic substrate, will now be discussed, with particular reference to FIGS. 6 and 7. FIG. 6 is a partially sectional elevation of an inspection station 108 built in accordance with the second embodiment, and FIG. 7 is a horizontal cross-sectional view of the apparatus of FIG. 6, taken as indicated by section lines VII—VII in FIG. 6.

Figure 7:
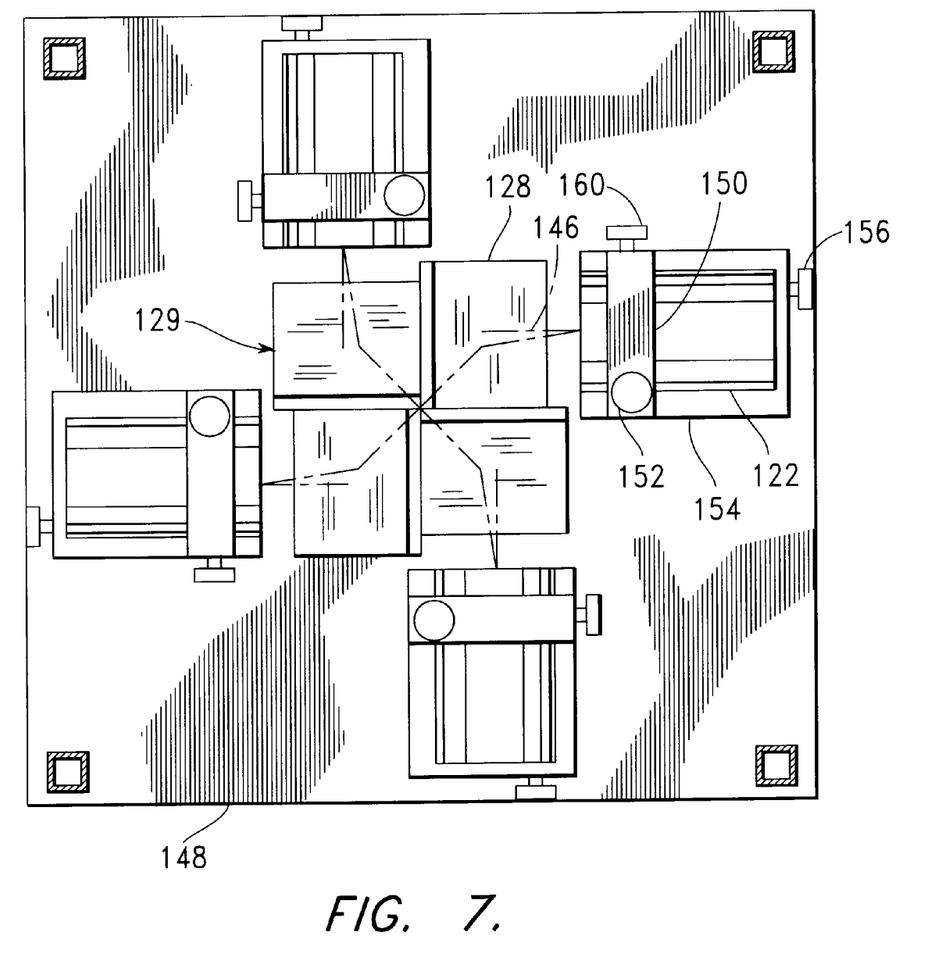
FIG. 7 is a horizontal cross-sectional view of the apparatus of FIG. 6, taken as indicated by section lines VII—VII in FIG. 6.

Referring to FIGS. 6 and 7, in the second embodiment 108 of the present invention, the substrate 10 is placed in an adjustable holder 110 atop a lens box 112, with the inner surface 114 of the substrate 10 to be inspected facing downward for imaging through a lens 116. The substrate surface 114 is illuminated by a ring light 118 extending partially around the lens 116, with light being supplied through a fiber optic cable 120 to pass through an annular window 122 extending around the upper surface of the ring light 118. The image from lens 116 passes through an aperture 124 at the bottom of lens box 112, to be received by four camera units 126 after reflection off four individual mirrors 128 forming part of a lower mirror assembly 129. This arrangement provides a magnification of, for example, 4.0 between the overlay pattern on surface 114 and the camera units 122.

When a different type of overlay pattern is to be inspected using this inspection station 108, the holder 110 is first adjusted with a ceramic substrate 10 or calibration substrate in place, so that the center of the overlay pattern is approximately aligned with the optical axis 130 of the lens 116. This is done with a deflecting mirror 132 moved rightward into the position indicated by dashed lines 134, so that the image of the overlay pattern is focussed on a ground glass surface 136 of a viewing screen 138. The surface 136 also includes various markings to indicate when the image is properly centered. The mirror 132 is mounted on a slide 140 allowing its movement in the directions of arrow 142 between a rightward position, in which the image of the overlay pattern is directed toward the viewing window 138, and a leftward position, in which the image proceeds downward to be viewed by the four camera units 128.

Each of the four camera units 128 is aligned to view a corner portion of the overlay pattern in an off axis manner. That is, a central image line 144 extending from the center of each image area of a camera unit 122 to the center of the CCD array (not shown) of the camera unit 122 extends through the lens 116, being angularly displaced from the optical axis 130 of the lens 116. However, each camera unit 128 is aligned so that, when reflection from a corresponding mirror 128 is considered, its optical axis 146 is parallel to the optical axis 130 of lens 116 and perpendicular to the surface 114 being imaged.

Each camera unit 128 is mounted to move along a base plate 148, on which mirror assembly 129 is mounted, by means of slides allowing movement in each of the three linear directions. Thus, each camera unit 128 is mounted to a vertical slide 150 allowing vertical motion in the directions of arrow 152, parallel to the optical axis 130. While such vertical movement changes the location of the image area of the camera unit, it does not effect focus. Each vertical slide 150 includes a knob 152 allowing manual adjustment. On the other hand, each vertical slide 150 is attached to a first horizontal slide 154, which allows movement of the camera unit 122 parallel to its optical axis 146. This movement is used to adjust the focus of the camera unit. Each of the first horizontal slides 154 has a knob 156 permitting manual adjustment. Each of the first horizontal slides 154 is in turn mounted on a second horizontal slide 158, which allows movement of the corresponding camera unit 122 in a horizontal direction parallel to the surface of the corresponding mirror 128, and perpendicular to the direction of motion allowed by the corresponding first horizontal slide 154. Each second horizontal slide 158 is moved by means of a knob 160.

Thus, when the size of the overlay pattern to be examined is changed, the image area of each camera is moved in a first direction by means of a vertical slide 150 and in a second direction, perpendicular to the first direction by means of a second horizontal slide 158. These movements should not affect the focus adjustment of the camera units 122. The focus of each camera unit 122 is adjusted by operating a first horizontal slide 154. Focussing movements may have a slight effect on the location of the image area on the overlay pattern, so adjustment of this position may be required after focussing.

The operation of the inspection station 108, built according to the second embodiment of this invention, is otherwise similar to the operation of the inspection station 8, built according to the first embodiment of this invention, which has been described in detail in reference to FIGS. 1–5. Generally, the camera units 122 of inspection station 108 cannot view the edges of ceramic substrate 10, since they are aimed a corner portions of an overlay pattern which is substantially smaller than the substrate. Thus, other markings are used to determine the alignment of the pattern.

Figure 8:
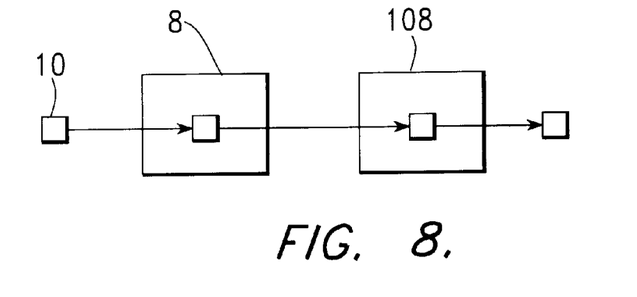
FIG. 8 is a block diagram of a inspection apparatus, including the inspection stations of FIGS. 1 and 6, for inspecting overlay patterns on both sides of a number of ceramic substrates.

FIG. 8 is a block diagram of a inspection apparatus for inspecting overlay patterns on both sides of a number of ceramic substrates 10. This apparatus includes an inspection station 8, built as described above in reference to FIGS. 1–5 in accordance with the first embodiment of the present invention, for inspecting the exterior side of the substrate 10 and an inspection station 108, built as described above in reference to FIGS. 6 and 7, in accordance with the second embodiment of the present invention, for inspecting the interior side of the substrate 10.

While the invention has been described in its preferred forms or embodiments with some degree of particularity, it is understood that this description has been given only by way of example and that numerous changes in the details of construction, fabrication and use, including the combination and arrangement of parts, may be made without departing from the spirit and scope of the invention.

What is claimed is:

1. Apparatus for determining characteristics of a visible pattern on a substrate during an inspection process, wherein said apparatus comprises:

a holder holding said substrate stationary during said inspection process, wherein said holder is divided into quadrants for engaging corners of said substrate, with a first quadrant being stationary, with a second quadrant being movable in a first direction in alignment with said first quadrant, with a third quadrant being movable in a second direction, perpendicular to said first direction, in alignment with said first quadrant, and with a fourth quadrant being movable in alignment with said second and third quadrants;

a plurality of camera units aimed at said visible pattern, wherein each camera unit within said plurality thereof is aimed at a different field of view in a spaced-apart relationship with fields of view of each other camera unit within said plurality thereof, and wherein each camera unit within said plurality thereof produces an electronic camera output signal indicative of features of a portion of said visible pattern during said inspection process, wherein said plurality of camera units includes four camera units, each of which has a field of view including a corner of a rectangular portion of said visible pattern, wherein a first camera unit is held stationary with said first quadrant, with a field of view of said first camera unit extending along a portion of said substrate held within said first quadrant, wherein a second camera unit is moved with said second quadrant, with a field of view of said second camera unit extending along a portion of said substrate held within said second quadrant, wherein a third camera unit is moved with said third quadrant, with a filed of view of said third camera unit extending along a portion of said substrate held within said third quadrant, and wherein a fourth camera unit is moved with said fourth quadrant, with a field of view of said fourth camera unit extending along a portion of said substrate held within said fourth quadrant; and computing means responsive to each said camera output signal during said inspection process for determining whether features of said visible pattern are within pre-determined limits, wherein said computing means is additionally operable during a calibration process, occurring before said inspection process, for determining calibration factors to be applied to said camera output signals during said inspection process, wherein each camera unit within said plurality thereof is held stationary during both said calibration process and said inspection process, wherein said computing means determines angular and linear locations of each camera unit within said plurality thereof during said calibration process from said camera output signals indicative of features in pre-determined locations on said calibration substrate, and wherein said computing means determines an overall size of said visible pattern from said camera output signals from said four camera units.

2. The apparatus of claim 1, additionally comprising:

a first illumination source held stationary with said first quadrant;

a second illumination source moving with said second quadrant;

a third illumination source moving with said third quadrant; and a forth illumination source moving with said third quadrant.

3. Apparatus for determining characteristics of a visible pattern on a substrate during an inspection process, wherein said apparatus comprises:

a holder holding said substrate stationary during said inspection process;

a plurality of camera units aimed at said visible pattern, wherein each camera unit within said plurality thereof is aimed at a different field of view in a spaced-apart relationship with fields of view of each other camera unit within said plurality thereof, wherein each camera unit within said plurality thereof is held stationary during said inspection process, and wherein each cameral unit within said plurality thereof produces an electronic camera output signal indicative of features of a portion of said visible pattern during said inspection process, wherein said plurality of camera units includes four camera units, each of which has a field of view including a corner of a rectangular portion of said visible pattern;

a single lens through which each said camera unit is aimed toward said visible pattern;

a mirror structure including four mirrors between said lens and said four camera units, with said four camera units being arrayed around said mirror structure, and with each mirror in said mirror structure reflecting an image of a portion of said visible pattern to a different camera unit within said plurality of camera units; and computing means responsive to each said camera output signal during said inspection process for determining whether features of said visible pattern are within pre-determined limits, wherein said computing means determines an overall size of said visible pattern from camera output signals from said four camera units.

4. The apparatus of claim 3:

wherein each said camera unit is movable for focusing in a focussing direction parallel to an optical axis thereof and wherein each said camera unit is movable for moving said field of view of said camera unit, with said camera unit being moveable in a first scanning direction parallel to an optical axis to said single lens, and in a second scanning direction perpendicular to said focussing direction and said first scanning direction.

5. A process for determining characteristics of a visible pattern on a substrate through the use of inspection apparatus including a plurality of camera units aimed at said visible pattern, wherein said process includes the steps of:

a) with each camera unit within said plurality thereof exposed to a portion of a calibration substrate having a pre-determined pattern, being aimed at a different field of view in a spaced apart relationship with fields of view of each other camera unit within said plurality thereof, determining correction factors for each individual camera, with said correction factors including distortion occurring within a lens in said camera unit and angular position of said camera unit;

b) with each camera unit within said plurality thereof exposed to a portion of said calibration substrate, being aimed at a different field of view in a spaced apart relationship with fields of view of each other camera unit within said plurality thereof, determining a frame of reference mapping pixel locations of said camera units to locations of actual features of said pre-determined pattern; and c) with each camera unit within said plurality thereof exposed to said visible pattern on said substrate, being aimed at a different field of view in a spaced apart relationship with fields of view of each other camera unit within said plurality thereof, determining characteristics of said visible pattern through the use of said frame of reference.

6. The process of claim 5, wherein said substrate and each camera unit in said plurality thereof are held stationary during said steps (a) through (c).

7. The process of claim 6, wherein said plurality of camera units includes four camera units, each of which has a field of view including a corner of a rectangular portion of said visible pattern, and said computing means determines an overall size of said visible pattern from camera output signals from said four camera units.

8. A computer readable medium having recorded thereon code executable within a computing system for controlling a process for determining characteristics of a visible pattern on a substrate through the use of inspection apparatus including a plurality of camera units aimed at said visible pattern, wherein said process includes the steps of:

a) with each camera unit within said plurality thereof exposed to a portion of a calibration substrate having a pre-determined pattern, being aimed at a different field of view in a spaced apart relationship with fields of view of each other camera unit within said plurality thereof, determining correction factors for each individual camera, with said correction factors including distortion occurring within a lens in said camera unit and angular position of said camera unit;

b) with each camera unit within said plurality thereof exposed to a portion of said calibration substrate, being aimed at a different field of view in a spaced apart relationship with fields of view of each other camera unit within said plurality thereof, determining a frame of reference mapping pixel locations of said camera units to locations of actual features of said pre-determined pattern; and c) with each camera unit within said plurality thereof exposed to said visible pattern on said substrate, being aimed at a different field of view in a spaced apart relationship with fields of view of each other camera unit within said plurality thereof, determining characteristics of said visible pattern through the use of said frame of reference.

9. The process of claim 7, wherein said computing means determines a location of said visible pattern relative to edges of said substrate from camera output signals from a camera unit within said four camera units.

* * * * *